United States Patent [19]

Cavazza

[11] Patent Number: 4,472,424
[45] Date of Patent: Sep. 18, 1984

[54] ESTERS OF 2-THENOYLMERCAPTOPROPIONYLGLYCINE WITH SUBSTITUTED HYDROXYBENZENES, PROCESS FOR THEIR PREPARATION AND PHARMACEUTICAL COMPOSITIONS CONTAINING SAME

[75] Inventor: Claudio Cavazza, Rome, Italy

[73] Assignee: Sigma-Tau Industrie Farmaceutiche Riunite S.p.A., Rome, Italy

[21] Appl. No.: 391,741

[22] Filed: Jun. 24, 1982

[30] Foreign Application Priority Data

Jul. 2, 1981 [IT]  Italy ................... 48807 A/81

[51] Int. Cl.$^3$ .................. A61K 31/38; C07D 333/24
[52] U.S. Cl. ........................ 424/275; 549/71; 549/72
[58] Field of Search .................. 549/72, 71; 424/275

[56] References Cited

U.S. PATENT DOCUMENTS 4,363,920 12/1982 Viscardi ........................ 549/72

FOREIGN PATENT DOCUMENTS 0044504 7/1980 European Pat. Off. .............. 549/72

OTHER PUBLICATIONS

Wagner et al., Synth. Org. Chem., (1965), p. 482.

*Primary Examiner*—Alan Siegel
*Attorney, Agent, or Firm*—Ladas & Parry

[57] ABSTRACT

Esters of 2-thenoylmercaptopropionylglycine with substituted hydroxybenzenes, having general formula

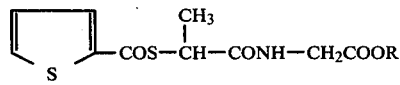

wherein R is p-acetamidophenyl, p-propyloxy carbophenyl or o-alkyloxycarbophenyl wherein the oxyalkyl radical contains 1-4 carbon atoms, are prepared by reacting 2-thenoylmercaptopropionylglycine with an alkylchloroformate thus obtaining a mixed anhydride which is reacted with the proper substituted hydroxybenzene selected among p-hydroxybenzeneacetamide, propyl p-hydroxybenzoate and alkyl o-hydroxybenzoate. These esters are useful therapeutical agents as mucolytic and antiinflammatory agents.

8 Claims, No Drawings

ESTERS OF 2-THENOYLMERCAPTOPROPIONYLGLYCINE WITH SUBSTITUTED HYDROXYBENZENES, PROCESS FOR THEIR PREPARATION AND PHARMACEUTICAL COMPOSITIONS CONTAINING SAME

The present invention relates to novel class of esters of 2-thenoylmercaptopropionylglycine with substituted hydroxybenzenes, having general formula (I)

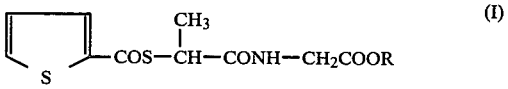

wherein R is a radical selected from the group consisting of p-acetamidophenyl, p-propyloxy carbophenyl and o-alkyloxycarbophenyl wherein the oxyalkyl radical contains 1–4 carbon atoms and is preferably methoxy or ethoxy.

The present invention also relates to a process for preparing these esters and to the pharmaceutical compositions containing same.

Specifically, the class of compounds having general formula (I) comprises the following esters:

(1) propyl p-(2-thenoylmercaptopropionyl glyciloxy) benzoate;
(2) p-(2-thenoylmercaptopropionyl glyciloxy) acetamido benzene;
(3) methyl o-(2-thenoylmercaptopropionyl glyciloxy) benzoate;
(4) ethyl o-(2-thenoylmercaptopropionyl glyciloxy) benzoate;
(5) propyl o-(2-thenoylmercaptopropionyl glyciloxy) benzoate; and
(6) butyl o-(2-thenoylmercaptopropionyl glyciloxy) benzoate.

Esters of mercaptopropionylglycine with a substituted hydroxybenzene, specifically guaiacol, are already known (in this regard, see the European Patent Application No. 79830052.1 filed in the name of the same applicant of this patent).

It is also known that these compounds possess pharmacological activity as mucolytic agents.

Although these known compounds are endowed with excellent mucolytic properties whilst they do not increase the bronchial secretion, some of these esters are, however, insufficiently stable. Consequently, the pharmaceutical compositions containing these esters can release an unpleasant smell even after a comparatively short storage period, thus unfavourably affecting both the user and the therapeutical effectiveness of the compositions.

This drawback becomes even worse when the compositions are stored and used in tropical countries. A further drawback of some of the known guaiacol esters is that they are oily or pitchy substances, which makes it difficult the processing and compounding thereof.

It has now been found that the novel esters having general formula (I), in addition to exhibiting excellent mucolytic activity with no increase in bronchial secretion, are remarkably more stable than the known guaiacol esters and, furthermore, are solid, powdery substances, which can be easily processed and compounded.

The process for preparing the esters having general formula (I) comprises the following steps:

(a) reacting 2-thenoylmercaptopropionylglycine with an alkylchloroformate having general formula ClCOOR' wherein R' is alkyl having from 1 to 4 carbon atoms, thus obtaining the corresponding mixed anhydride; and (b) reacting the mixed anhydride of step (a) with a substituted hydroxybenzene selected in the class consisting of p-hydroxybenzenacetamide, propyl p-hydroxybenzoate and alkyl o-hydroxybenzoate wherein the alkyl radical has 1–4 carbon atoms.

More specifically:

As regards step (a), 2-thenoylmercaptopropionylglycine and an anhydrous, organic base, preferably selected between triethylamine and pyridine, are added in equimolecular amounts to an inert organic solvent, such as methylene chloride, tetrahydrofurane and dioxane. The resulting solution is cooled to a temperature generally comprised between about 0° C. and about −20° C. To this solution, a solution of alkylchloroformate dissolved in the same organic solvent used for 2-thenoylmercaptopropionylglycine is slowly added under stirring. The alkylchloroformate amount is preferably equimolar with respect to 2-thenoylmercaptopropionylglycine.

The resulting reaction mixture is kept under stirring for about 10–60 minutes, thus obtaining the mixed anhydride that can be either isolated or directly utilized in solution form in the subsequent process step (b).

As regards step (b), to the mixed anhydride solution kept at a temperature comprised between about +5° C. and −20° C., a solution of substituted hydroxybenzene and of anhydrous, organic base (e.g. triethylamine) in an inert, anhydrous, organic solvent, such as methylene chloride, tetrahydrofurane and dioxane, is added. The resulting reaction mixture is kept under stirring at low temperature (from about +5° C. to about +15° C.) for about 15–60 minutes, and subsequently at room temperature for about 2–24 hours.

When the reaction is carried out in a water-insoluble solvent (e.g. $CH_2Cl_2$), the solution is washed with $H_2O$, diluted HCl, $H_2O$ to neutrality, dried and concentrated under vacuum. When other solvents are used (for instance tetrahydrofurane and dioxane), the product is isolated after filtration of the organic base hydrochloride and concentration of the solvent under vacuum.

The following non-limiting examples illustrate the preparation of some compounds of the present invention.

EXAMPLE 1

Preparation of propyl p-(2-thenoylmercaptopropionyl glyciloxy) benzoate.

5.4 grams (0.020 moles) of 2-thenoylmercaptopropionylglycine and 2.0 grams (0.020 moles) of triethylamine were added to 50 ml of tetrahydrofurane.

The temperature of the resulting mixture was brought to 0° C., then a solution of ethylchloroformate (2.2 grams; 0.020 moles) in 10 ml of tetrahydrofurane was slowly added. Subsequently, the following solution was slowly added:
triethylamine: 2.0 g; (0.020 moles)
tetrahydrofurane: 20 ml
propyl p-hydroxybenzoate: 3.6 g (0.020 moles).

The reaction mixture was kept under stirring at 5° C. for 1 hour and then at room temperature for 4 hours. The reaction mixture was filtered. The filtrate was brought to dryness and extracted several times with warm hexane; a yellowish oil precipitated by cooling. The oil was crystallized from hexane.

Melting point: 94°–95° C.

T.L.C.: silica gel, toluene: ether (60:40).

| H.P.L.C. | | |
|---|---|---|
| column | Lichrosorb RP | 18 |
| eluant | $H_2O$ | 65 |
| | $CH_3CN$ | 35 |
| | $CH_3COOH$ | 1 |
| U.V. detector = 254 mµ | | |

NMR (DMSO) δ=1.03 (t,3H,$CH_2$—$\underline{CH_3}$); 1.60 (d,3H,CH—$\underline{CH_3}$); 1.73 (m,2H,$\underline{CH_2}$—$CH_3$); 4.23 (d,2H,NH—$\underline{CH_2}$); 4.30 (t,2H,$\underline{CH_2}$—$CH_2$—$CH_3$); 4.50 (q,1H,$\underline{CH}$—$CH_3$); 7.10–8.03 (m,3H,thiophene); 7.26–8.13 (d,4H, arom).

EXAMPLE 2

Preparation of p-(2-thenoylmercaptopropionyl glyciloxy) acetamidobenzene.

5.4 grams (0.020 moles) of 2-thenoylmercaptopropionylglycine were added to 50 ml of tetrahydrofurane. The temperature of the resulting mixture was brought to 0° C., then a solution of ethylchloroformate (2.2 grams; 0.020 moles) in 10 ml of anhydrous $CH_2Cl_2$ was slowly added. To the resulting solution, the following solution was slowly added:

p-hydroxy acetamidobenzene: 3.0 g (0.020 moles)
triethylamine: 2.0 g (0.020 moles)
tetrahydrofurane: 20 ml.

The reaction mixture was kept under stirring at 5° C. for 1 hour and then at room temperature for 4 hours. The solid product which formed was filtered off, washed with water and then crystallized from methanol. A solid, crystalline, white product having melting point of 203°–204° C. was obtained.

T.L.C.: silica gel, toluene:ether 60:40.

| H.P.L.C.: | | |
|---|---|---|
| column: | Lichrosorb RP | 18 |
| eluant: | $H_2O$ | 65 |
| | $CH_3CN$ | 35 |
| | $CH_3COOH$ | 1 |
| U.V. detector = 250 mµ | | |

NMR (DMSO) δ=1.58 (d,3H,CH—$\underline{CH_3}$); 2.15 (s,3H,$COCH_3$); 4.26 (d,2H,$CH_2$); 4.56 (q,1H,$\underline{CH}$—$CH_3$); 7.20–7.80 (d,4H, arom.); 7.26–8.30 (m,3H, thiophene); 9.05 (t,1H,$\underline{NH}$—$CH_2$); 10.26 (s,1H,NH—CO).

The acute toxicity, the expectorant and mucolytic activities and the effect on ciliar motility of compounds of formula (I) were studied.

Acute toxicity

LD50 of the compounds of formula (I) assessed with the Weil method ("Tables for convenient calculation of median effective dose (LD50 or ED 50) and instructions in their use", Biometrics, 249–253, 1952), by e.p. administration in mouse is shown in Table 1.

TABLE 1

| LD50 and fiducial limits, mg/Kg e.p., of the compounds of formula (I). Weil method N = 4 K = 4 | | |
|---|---|---|
| Compound | DL50 | fiducial limits |
| (1) | 1580 | (1260–1900) |
| (2) | 1930 | (1620–2240) |
| (3) | 1780 | (1440–2120) |
| (4) | 2150 | (1900–2400) |
| (5) | 2080 | (1800–2350) |
| (6) | 1800 | (1500–2100) |

Expectorant activity

The tests were carried out on male rabbits, weighing 2–3 Kg, anesthetized with ethyl urethane, by following the method disclosed by Perry et al. (J. Pharm. Exp. Ther. 73, 65, 1941).

The anesthetized animals, strapped head downward to an operating table at an inclination of 60°, had a cannula inserted in their trachea. Each cannula was connected to a feeding device which delivered a steady flow-rate of pre-heated air (36°–38° C.) at constant humidity (80%). At the lower end of each cannula, a graduated cylinder was fitted, wherein the bronchial secretion was collected. All of the animals breathed spontaneously and consequently they self-regulated the air intake suitable for normal respiration. After an hour following cannula insertion, the animals were administered orally (by stomach tube) the compounds of general formula (I) dissolved in distilled water at doses comprised between 20 and 40 mg. Each dose of drug was administered to 5 animals. The control animals (8) were given water only. The amount of secretion was determined after 1, 2 and 4 hours from administration. The results, summarized in Table 2, show that the compounds of general formula (I) do not exert expectorant activity.

Mucolytic activity

The tests were carried out in vitro by using the method disclosed by Morandini et al. (Lotta contro la tuberculosi 47, n. 4, 1977). A thromboelastograph was used to follow the variations induced by the compounds of general formula (I) and acetylcysteine on the rheological properties of human sputum. The results thereof, summerized in Table 3, show that the compounds of formula (I) bring about a greater decrease of human sputum density than that induced by acetylcysteine.

Effect on ciliary activity

The ability of the compounds of formula (I) to affect the ciliary motility was studied by observing with the microscope the ciliary movement of rat trachea rings soaked in solutions of the test compounds.

By this technique it is possible to study, with relation to compound concentration and contact time, the ciliary movement block provoked by the tests compounds, which is related to mucus clearance from ciliary epithelium.

Substances to be used in the form of solutions must allow the foregoing block not to take place in less than fifteen minutes from contact.

2% aqueous solutions of the compounds of formula (I) provoked the ciliary movement block to take place in 18–20 minutes.

Antitussive activity

The cough-inducing irritation was studied in guinea pigs by exposing the experimental animals to an environment wherein a 10% citric acid solution was atomized by an aerosol device kept at a steady pressure with compressed air. The experimental animals were placed in a glass-walled chamber which was connected to an electrical recording apparatus suitable for counting coughs.

The period of exposure to the cough-inducing aerosol was 10 minutes. The experimental animals were subjected to a control test seven days before they were orally administered 200 mg/Kg of the compounds. The results of some experiments carried out on treated vs. control animals, summarized in Table 4, show that the compounds with general formula (I) demonstrate antitussive activity after a single administration of 200 mg/Kg one hour before the beginning of the test.

TABLE 2

Effect of compounds of general formula (I) on bronchial secretion

| Compounds | Percentage variations ± s.e. of bronchial secretion versus basal values at the following time intervals after administration | | |
|---|---|---|---|
| | 1 hour | 2 hours | 4 hours |
| Control (H$_2$O) | +1.2 ± 0.04 | +2.1 ± 0.04 | +3.2 ± 0.05 |
| (1) | +0.9 ± 0.05 | +2.1 ± 0.01 | +3.8 ± 0.06 |
| (2) | +0.8 ± 0.03 | +1.2 ± 0.04 | +2.5 ± 0.07 |
| (3) | +0.3 ± 0.05 | +0.9 ± 0.05 | +1.4 ± 0.08 |
| (4) | +0.8 ± 0.03 | +1.9 ± 0.06 | +3.0 ± 0.04 |
| (5) | +0.9 ± 0.06 | +1.7 ± 0.05 | +3.2 ± 0.06 |
| (6) | +0.5 ± 0.04 | +1.0 ± 0.06 | +1.9 ± 0.04 | n = 6 animals per group

TABLE 3

Mucolytic activity in vitro of compounds of general formula (I) and acetylcysteine; modifications of human sputum density.

| Compounds | Percentage drop ± s.e. of the tracing versus maximum peak (*) after addition of 1 ml of a 10% solution of the test compounds at the dilution indicated | |
|---|---|---|
| | 1/30 | 1/60 |
| (1) | 75 | 60 |
| (2) | 86 | 65 |
| (3) | 85 | 65 |
| (4) | 82 | 60 |
| (5) | 78 | 57 |
| (6) | 75 | 55 |
| Acetylcysteine | 75 | 22 |

(*) Mucolytic activity index

As experimentally shown, the compounds of this invention significantly modify the rheological properties of sputum. On perusal of the obtained results a decrease in sputum density at the larger doses (or lower dilutions) and at the smaller doses (or higher dilutions) constantly higher than that provoked by acetylcysteine, is detected. On the other hand one of the compounds increases bronchial secretion nor is able to block the ciliary movement of the epithelium of trachea ring preparations in time intervals shorter that those permitted.

TABLE 4

Antitussive action in guinea-pigs: number of coughs and percentage of inhibition before and after treatment with the compounds of formula (I)

| Number of Animals | Compound | Number of coughs | | % Inhibition |
|---|---|---|---|---|
| | | before treatment | after treatment | |
| 10 | — | 45 | 44 | 3 |
| 6 | 1 | 61 | 39 | 37 |
| 6 | 2 | 55 | 30 | 46 |
| 6 | 3 | 60 | 31 | 49 |
| 6 | 4 | 62 | 30 | 52 |
| 6 | 5 | 54 | 28 | 49 |
| 6 | 6 | 49 | 25 | 49 |

The compounds of the present invention are therapeutically useful for the treatment of the diseases of the respiratory tract. The patients in need thereof will be orally or parenterally administered a therapeutically effective amount of an ester of general formula (I).

The dose of guaiacol ester of general formula (I) orally or parenterally administered will be generally comprised between about 15 and about 70 mg/Kg of body weight/day, although larger or smaller doses can be administered by the attending physician having regard to the age, weight and general conditions of the patient, utilizing sound professional judgement.

In practice, the guaiacol esters are orally or parenterally administered in any of the usual pharmaceutical forms which are prepared by conventional procedures well-known to those persons skilled in the pharmaceutical technology. These forms include solid and liquid oral unit dosage forms such as tablets, capsules, solutions, syrups and the like as well as injectable forms, such as sterile solutions for ampoules and phials. Hereinbelow some non-limiting examples of compositions suitable for oral or parenteral administration are given.

Pharmaceutical Compositions

In all the following compositions, the "active ingredient" is, by way of exemplification, p-(2-theoylmercaptopropionyl glyciloxy) acetamido benzene.

| Ampoules for aerosol administration or intramuscular administration | |
|---|---|
| Each ampoule contains: | |
| active ingredient | 0.40 g |
| sodium metabisulfite | 10 mg |
| pyrogen-fre, distilled water | 3 ml |
| Syrup | |
| active ingredient | 4.0 g |
| sorbitol, 70 percent | 15 g |
| sucrose | 50 g |
| ethanol | 1 ml |
| p-hydroxybenzoate | 0.2 mg |
| flavoring agents | 0.5 ml |
| distilled water | q.s. to 100 ml |
| saccharin | 0.20 g |
| Suppositories for Adults | |
| active ingredient | 0.40 g |
| sodium metabisulfite | 0.020 g |
| excipients q.s. to 1 suppository | |
| Pediatric Suppositories | |
| active ingredient | 0.20 g |
| sodium metabisulfite | 0.010 g |
| excipient q.s. to 1 suppository | |
| Suppositories for unweaned babies | |
| active ingredient | 0.10 g |
| sodium metabisulfite | 0.005 g |
| excipient q.s. to 1 suppository | |
| Single-dose sachet (5 g) | |
| Each 100 grams contains: | |

| -continued | |
|---|---|
| active ingredient | 3.80 g |
| saccharin | 0.20 g |
| orange flavour | 0.5 g |
| orange lyophilyzate | 10 g |
| sucrose, balance to 100 grams | |

What is claimed is:

1. Ester of 2-thenoylmercaptopropionylglycine of general formula (I)

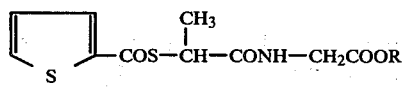

wherein R is a radical selected from the group consisting of p-acetamidopheny, p-propyloxycarbophenyl and o-alkyloxycarbophenyl wherein the oxyalkyl radical contains 1-4 carbon atoms and is preferably methoxy or ethoxy.

2. As ester of claim 1, propyl p-(2-thenoylmercaptopropionyl glyciloxy) benzoate.

3. As ester of claim 1, p-(2-thenoylmercaptopropionyl glyciloxy) acetamidobenzene.

4. As ester of claim 1, methyl o-(2-thenoylmercaptopropionyl glyciloxy) benzoate.

5. As ester of claim 1, ethyl o-(2-thenoylmercaptopropionyl glyciloxy) benzoate.

6. As ester of claim 1, propyl o-(2-thenoylmercaptopropionyl glyciloxy) benzoate.

7. As ester of claim 1, butyl o-(2-thenoylmercaptopropionyl glyciloxy) benzoate.

8. A pharmaceutical composition having mucolytic and antiinflammatory activities characterized in that it contains, as active ingredient, an ester of 2-thenoylmercaptopropionylglycine having general formula (I)

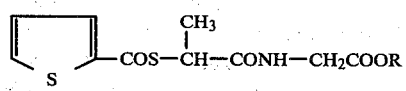

wherein R is a radical selected from the group consisting of p-acetamidobenzyl, p-propyloxycarbonyl and o-alkyloxycarbonyl wherein the oxyalkyl radical contains 1-4 carbon atoms and is preferably methoxy or ethoxy, and a pharmacologically acceptable excipient.

* * * * *